(12) United States Patent
Lee

(10) Patent No.: US 7,708,409 B1
(45) Date of Patent: May 4, 2010

(54) CONTROLLING BEAM INTENSITY IN OPHTHALMIC ILLUMINATION SYSTEMS USING SERIAL ROTATABLE SHAPES

(75) Inventor: Robin Michael Lee, Linton (GB)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/332,806

(22) Filed: Dec. 11, 2008

(51) Int. Cl.
*A61B 3/10* (2006.01)

(52) U.S. Cl. ..................................... 351/221
(58) Field of Classification Search ............... 351/200, 351/221
See application file for complete search history.

(56) References Cited

U.S. PATENT DOCUMENTS 6,309,070 B1 * 10/2001 Svetliza et al. ............. 351/221
7,189,226 B2   3/2007 Auld et al. .................. 606/11
7,444,057 B2  10/2008 Dacquay et al. ............ 385/140

* cited by examiner

Primary Examiner—Huy K Mai
(74) Attorney, Agent, or Firm—Jeffrey B. Powers

(57) ABSTRACT

An ophthalmic illumination system includes planar shapes serially positioned in a path for a collimated beam, along an optical axis. The shapes are rotationally symmetric with one another relative to the optical axis. Each shape has a central rotational axis intersecting the optical axis. Generally wedge-shaped segments of the shapes are spaced apart around and converge at the optical axis to provide generally wedge-shaped apertures to the beam between the segments. The shapes are rotatable on the rotational axes along the optical axis to assume a plurality of configurations to vary intensity of the beam. The beam can fill spatial modes at substantially all radii of the optical fiber entrance pupil.

20 Claims, 3 Drawing Sheets

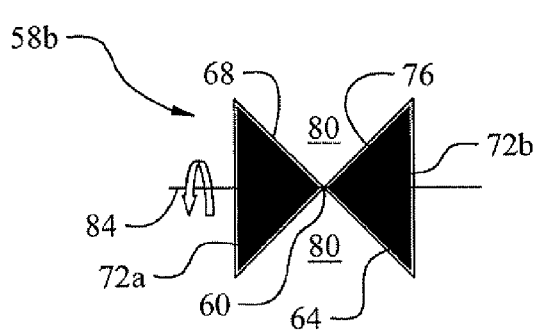 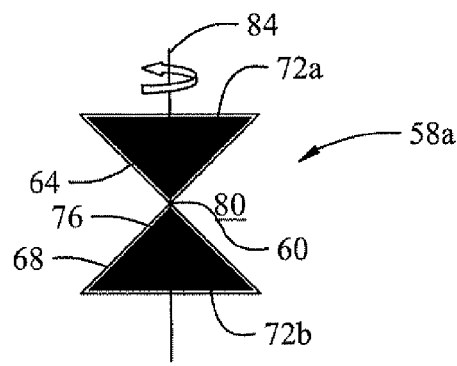
Fig. 3A    Fig. 3B
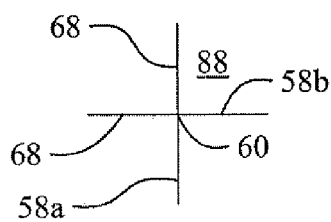 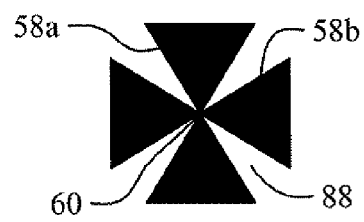 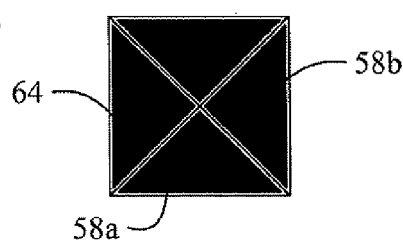
Fig. 4A    Fig. 4B    Fig. 4C
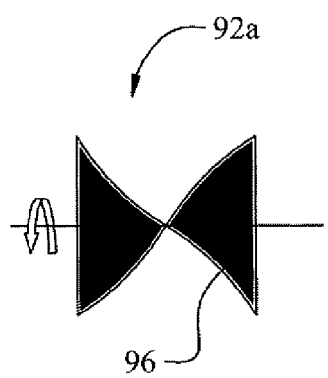 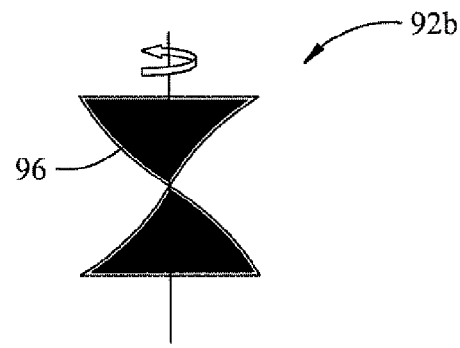
Fig. 5A    Fig. 5B

CONTROLLING BEAM INTENSITY IN OPHTHALMIC ILLUMINATION SYSTEMS USING SERIAL ROTATABLE SHAPES

FIELD

The present disclosure relates to ophthalmic illumination systems and more particularly to an ophthalmic illumination system in which planar shapes are serially positioned along an optical axis of a collimated beam and are rotatable to control intensity of the beam.

BACKGROUND

This section provides background information related to the present disclosure which is not necessarily prior art.

When ophthalmic surgery is performed, an ophthalmic illumination system is used to illuminate the interior of a patient's eye so that the surgeon may view the surgical site. In a typical ophthalmic illumination system, light is collimated and focused onto the entrance pupil of an optical fiber that transmits light to an opto-illuminator, or light probe. A tip of the probe is inserted into an incision in the eye.

It is highly desirable to be able to control the brightness of illumination at the surgical site. In illumination systems in which filament lamps have been used, electrical power to the light source may be reduced to lower the brightness of the source and accordingly the illumination of the site. Reducing the power, however, can change the color temperature of the light and affect the quality of illumination. Furthermore, intensities of new, high-brightness light sources such as zenon arc lamps typically are not easily controlled through electrical means.

SUMMARY

This section provides a general summary of the disclosure, and is not a comprehensive disclosure of its full scope or all of its features.

In one implementation, the present disclosure is directed to an ophthalmic illumination system including an optical fiber having an entrance onto which a collimated light beam may be focused for transmission to an ophthalmic light probe. A plurality of planar shapes are positioned in a path for the collimated beam. The shapes, which provide discrete rotational symmetry, are configured serially along an optical axis of the system and axially symmetric with one another relative to the optical axis. Each shape has a central rotational axis that intersects the optical axis. Each shape has a plurality of generally wedge-shaped segments spaced apart around and converging at the optical axis and configured to provide generally wedge-shaped apertures to the beam between the segments. The shapes are rotatable on the rotational axes along the optical axis to assume a plurality of configurations, including an open configuration in which faces of the shapes are parallel to the optical axis and a closed configuration in which faces of the shapes are normal to the optical axis.

In another implementation, the disclosure is directed to an ophthalmic illumination system including a light source and light collection optics through which a beam from the light source may be collimated and focused onto the entrance of an optical fiber for transmission to an ophthalmic light probe. The light collection optics includes a plurality of planar shapes positioned serially in a path for the beam. Each shape is centered on an optical axis of the light collection optics through a rotational axis of the shape that intersects the optical axis. The shapes are rotationally symmetric with one another relative to the optical axis. The rotational axes of the shapes intersect the optical axis at regular degree intervals around the optical axis. Each shape has a plurality of generally tapered segments each having a tapered end at the optical axis and spaced apart to provide generally tapered apertures to the beam. The shapes are rotatable on the rotational axes along the optic axis to selectively vary an intensity of the beam.

In yet another implementation, the disclosure is directed to a method of using an ophthalmic illumination system having a light source and light collection optics for collimating and focusing a beam onto the entrance of an optical fiber for transmission to an ophthalmic light probe. The method includes moving a plurality of planar shapes serially positioned in a path of the collimated beam, each shape centered on an optical axis of the light collection optics through a rotational axis of the shape that intersects the optical axis. The shapes are rotationally symmetric with one another relative to the optical axis. The rotational axes of the shapes intersect the optical axis at regular degree intervals around the optical axis. Each shape has a plurality of generally tapered segments each having a tapered end at the optical axis and spaced apart to provide generally tapered apertures to the beam. At least one of the following is performed: rotating the shapes on the rotational axes, and translating the shapes along the optic axis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3A and 3B are frontal views of shapes configured for inclusion in light collection optics of an ophthalmic illumination system in accordance with one implementation of the disclosure;

FIG. 4A is a frontal view of shapes in an open configuration in light collection optics of an ophthalmic illumination system in accordance with one implementation of the disclosure;

FIG. 4B is a frontal view, taken along lines 4B-4B of FIG. 2, of shapes in a "cross" configuration in light collection optics of an ophthalmic illumination system in accordance with one implementation of the disclosure;

FIG. 4C is a frontal view of shapes in a closed configuration in light collection optics of an ophthalmic illumination system in accordance with one implementation of the disclosure; and FIGS. 5A and 5B are frontal views of shapes configured for inclusion in light collection optics of an ophthalmic illumination system in accordance with one implementation of the disclosure.

DETAILED DESCRIPTION

Example embodiments will now be described more fully with reference to the accompanying drawings.

Figure 1:
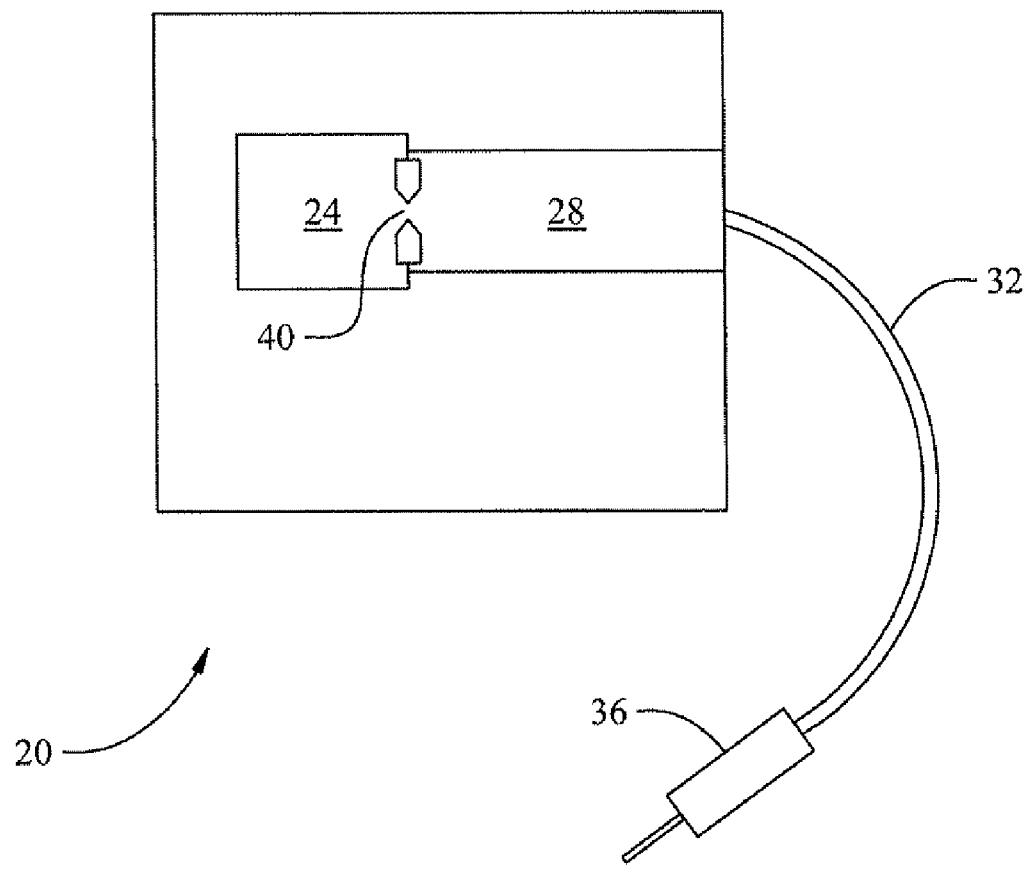
FIG. 1 is a diagram of an ophthalmic illumination system in accordance with one implementation of the disclosure.

A diagram of an ophthalmic illumination system in accordance with one implementation of the disclosure is indicated generally in FIG. 1 by reference number 20. A light source 24 provides light that is collected, collimated, and refocused via light collection optics 28 for transmission through an optical fiber 32 to a light probe 36. In the present exemplary embodiment the light source 24 is a xenon arc lamp that produces an arc 40, although a filament lamp or other type of light source could be used.

Figure 2:
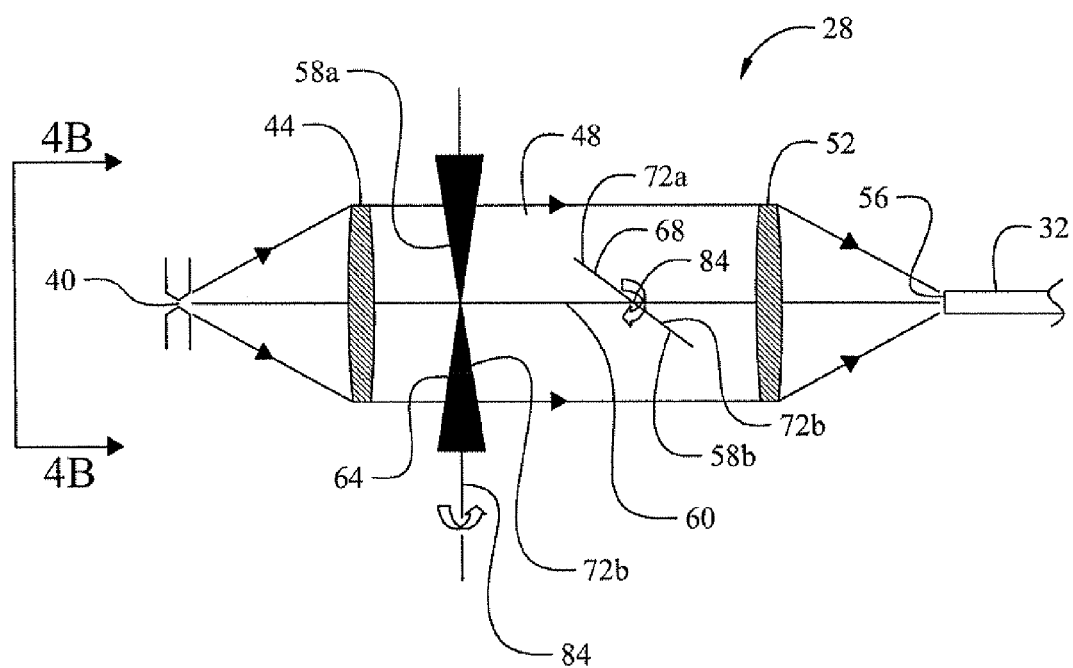
FIG. 2 is a diagram of light collection optics of an ophthalmic illumination system in accordance with one implementation of the disclosure.

Light collection optics 28 are shown in greater detail in FIG. 2. Light from the xenon arc 40 is received by a collecting and collimation means 44, e.g., a lens and/or mirror. The collimated beam travels a path 48 to a refocusing means 52, e.g., a lens, that refocuses the beam onto an entrance 56 of the optical fiber 32. In some configurations there may be some re-magnification of the source size such that the fiber 32 is slightly overfilled with respect to the extent of the refocused source and with respect to the numerical aperture (NA) of the fiber 32. While the present example is described in relation to a collimated beam, the present invention is equally applicable using a diverging beam. If a diverging beam is used, the shapes should be sealed by the divergence angle of the bean so that the projected shadows tessellate.

Referring now to FIGS. 2, 3A and 3B, a plurality of planar shapes collectively referred to by reference number 58 are positioned serially in the path 48 along an optical axis 60 of the light collection optics 28. In the present example, two shapes 58a and 58b are provided, although in other configurations more than two shapes may be provided. "Planar" means flat and thin so as to be almost two-dimensional. Accordingly, each shape 58 has two faces 64 and a thin edge 68. The shapes 58 are rotationally symmetric relative to the optical axis 60.

FIGS. 3A and 3B are frontal views of the shapes 58a and 58b. Each shape 58 has a plurality of generally wedge-shaped, or tapered, segments collectively referred to by reference number 72. In the present example, two segments 72a and 72b are provided, although in other configurations more than two segments may be provided. The segments 72 are equally spaced apart around the optical axis 60 and have tapered ends 76 converging at the optical axis 60. In the present configuration, the segments 72a and 72b are spaced apart by 180 degrees. A plurality of generally wedge-shaped, or tapered, apertures 80 are provided between the segments 72. In the present example, each shape 58 provides two apertures 80.

Each shape 58 is centered on the optical axis 60. Specifically, each shape 58 has a central rotational axis 84 that intersects the optical axis 60. The rotational axes 84 intersect the optical axis 60 at regular degree intervals around the optical axis 60. In the present example, the interval between the axes 84 of the shapes 58a and 58b is 90 degrees. As another example, in a configuration having four shapes, the rotational axes of the shapes intersect the optical axis at 45-degree intervals.

The shapes 58 are rotatable on their axes 84 along the optical axis 60 to selectively vary the intensity of the collimated light beam. Intensity of the light can be varied between approximately zero percent and approximately 100 percent of full brightness. The shapes 58 are movable to assume a plurality of configurations, including but not limited to an open configuration in which the faces 64 of the shapes are parallel to the optical axis 60. As shown in FIG. 4A, in the open configuration only the thin edges 68 of the shapes 58 are presented to the collimated beam. When the shapes 58 are in the open configuration, substantially maximum intensity of the beam is allowed to be focused onto the optical fiber entrance 56. As shown in FIGS. 2 and 4B, the shapes 58 are rotated to form a "cross" that blocks a portion of the beam from reaching the fiber entrance 56. Additionally or alternatively, the shapes 58 can be translated together and rotated to assume a closed configuration in which faces 64 of the shapes 58 are normal to the optical axis 60, thereby substantially completely obscuring the beam as shown in FIG. 4C.

By rotating the shapes 58 by angles between zero degrees and ninety degrees, a user of the system 20 can select a beam intensity from a range of brightness levels. At substantially all values of rotation of the shapes 58, e.g., as shown in FIG. 4B, light is allowed past the shapes 58 through wedges 88 at substantially all radii relative to the optical axis 60. Furthermore, the light allowed past the shapes 58 has a flux per radial annulus that is substantially proportional to the radius, i.e., substantially all spatial modes are equally filled.

As previously mentioned, more than two rotatable shapes are possible. For example, in one configuration four shapes may be provided that have forty-five-degree tapered ends and rotational axes every 45 degrees around the optical axis. Furthermore, shapes are not necessarily straight-edged. Shapes may be curved at least in part. For example, as shown in FIGS. 5A and 5B, tessellating shapes 92a and 92b include curved edges 96.

Because an optical fiber in a typical illumination system is short (e.g., between one and two meters of 100-micrometer core fiber), it is highly advantageous to fill the spatial mode structure of the fiber at the point of illumination. Otherwise the resulting illumination at the output end of the fiber might cause undesirable spatial structure, e.g., light and dark patches and streaks. Advantageously, in the foregoing illumination system, spatial modes are filled at substantially all radii of the optical fiber entrance pupil, in contrast to many existing mechanical shutter systems.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An ophthalmic illumination system comprising:
    an optical fiber having an entrance onto which a light beam may be focused for transmission to an ophthalmic light probe;
    a plurality of substantially planar shapes positioned in a path for the collimated beam, the shapes configured serially along an optical axis of the system and rotationally symmetric with one another relative to the optical axis, each shape having a central rotational axis that intersects the optical axis;
    each shape having a plurality of generally wedge-shaped segments spaced apart around and converging at the optical axis and configured to provide generally wedge-shaped apertures to the beam between the segments; and the shapes rotatable on the rotational axes along the optical axis to assume a plurality of configurations including an open configuration in which faces of the shapes are parallel to the optical axis and a closed configuration in which faces of the shapes are normal to the optical axis.

2. The ophthalmic illumination system of claim 1, wherein the rotational axes of the shapes intersect the optical axis at regular degree intervals around the optical axis.

3. The ophthalmic illumination system of claim 2 comprising two planar shapes, each degree interval being ninety (90) degrees.

4. The ophthalmic illumination system of claim 2 comprising four planar shapes, each degree interval being forty-five (45) degrees.

5. The ophthalmic illumination system of claim 1, wherein the open configuration allows a substantially maximum intensity of the beam to be focused onto the optical fiber and the closed configuration blocks a substantially maximum intensity of the beam.

6. The ophthalmic illumination system of claim 1, configured to allow at least some of the beam through the apertures at substantially all radii of the beam relative to the optical axis.

7. The ophthalmic illumination system of claim 1, wherein the segments tessellate and comprise curved edges.

8. The ophthalmic illumination system of claim 1, wherein the segments of one of the shapes are equally spaced apart around the optical axis.

9. An ophthalmic illumination system comprising:
a light source;
light collection optics through which a beam from the light source may be focused onto an entrance of an optical fiber for transmission to an ophthalmic light probe;
the light collection optics including a plurality of planar shapes positioned serially in a path for the collimated beam, each shape centered on an optical axis of the light collection optics through a rotational axis of the shape that intersects the optical axis, the shapes rotationally symmetric with one another relative to the optical axis, the rotational axes of the shapes intersecting the optical axis at regular degree intervals around the optical axis;
each shape having a plurality of generally tapered segments each having a tapered end at the optical axis and spaced apart to provide generally tapered apertures to the beam; and
the shapes rotatable on the rotational axes along the optic axis to selectively vary an intensity of the beam.

10. The ophthalmic illumination system of claim 9, wherein the shapes are movable between an open configuration in which faces of the shapes are parallel to the optical axis and a closed configuration in which faces of the shapes are normal to the optical axis.

11. The ophthalmic illumination system of claim 9, wherein each of the tapered ends of the segments has a ninety-degree taper.

12. The ophthalmic illumination system of claim 9, wherein each of the tapered ends of the segments has a forty-five-degree taper.

13. The ophthalmic illumination system of claim 12, comprising four shapes.

14. The ophthalmic illumination system of claim 9, wherein the shapes tessellate and comprise curved edges.

15. The ophthalmic illumination system of claim 9, wherein the rotational axes of the shapes intersect the optical axis at degree intervals equally spaced apart around the optical axis.

16. A method of using an ophthalmic illumination system having a light source and light collection optics for focusing a beam onto the entrance of an optical fiber for transmission to an ophthalmic light probe, the method comprising:
moving a plurality of planar shapes serially positioned in a path of the collimated beam, each shape centered on an optical axis of the light collection optics through a rotational axis of the shape that intersects the optical axis, the shapes rotationally symmetric with one another relative to the optical axis, the rotational axes of the shapes intersecting the optical axis at regular degree intervals around the optical axis, each shape having a plurality of generally tapered segments each having a tapered end at the optical axis and spaced apart to provide generally tapered apertures to the beam; and
the moving including rotating the shapes on the rotational axes.

17. The method of claim 16, the moving performed to selectively vary an intensity of the beam.

18. The method of claim 16, further comprising moving the shapes to an open configuration in which faces of the shapes are parallel to the optical axis.

19. The method of claim 16, further comprising moving the shapes to a closed configuration in which faces of the shapes are normal to the optical axis.

20. The method of claim 16, further comprising moving the shapes to allow light through the apertures at substantially all radii of the beam relative to the optical axis.

\* \* \* \* \*